United States Patent [19]

Nakagawa

[11] Patent Number: 5,641,393
[45] Date of Patent: Jun. 24, 1997

[54] HIGH-SILICA ZEOLITE SSZ-37 AND METHODS OF MAKING AND USING SAME

[75] Inventor: Yumi Nakagawa, Oakland, Calif.

[73] Assignee: Chevron U.S.A. Inc., San Francisco, Calif.

[21] Appl. No.: 512,603

[22] Filed: Aug. 8, 1995

Related U.S. Application Data

[63] Continuation-in-part of Ser. No. 380,233, Jan. 30, 1995, abandoned, which is a continuation of Ser. No. 243,603, May 16, 1994, abandoned, which is a continuation of Ser. No. 95,771, Jul. 21, 1993, abandoned, which is a division of Ser. No. 906,919, Jun. 30, 1992, Pat. No. 5,254,514.

[51] Int. Cl.⁶ .................... C10G 11/05; C10G 47/16; C10G 3/00; B01J 29/04
[52] U.S. Cl. .................... 208/46; 208/28; 208/109; 208/111; 208/118; 208/120; 502/61; 502/62; 502/64; 502/65; 502/66; 585/418; 585/420; 585/446; 585/481; 585/640; 585/533; 585/733; 585/752; 585/739
[58] Field of Search .................... 502/62, 61, 64, 502/65, 66; 423/709, 718; 208/111, 114, 118, 124, 120, 137, 138, 28, 46, 58, 109; 585/407, 446, 533, 733, 752, 739, 418, 420, 481

[56] References Cited

U.S. PATENT DOCUMENTS

| | | | |
|---|---|---|---|
| 4,589,976 | 5/1986 | Zones | 208/111 |
| 4,589,977 | 5/1986 | Zones | 208/111 |
| 4,963,337 | 10/1990 | Zones | 423/277 |
| 5,041,402 | 8/1991 | Casci et al. | 502/67 |
| 5,102,641 | 4/1992 | Casci et al. | 423/328 |
| 5,178,748 | 1/1993 | Casci et al. | 208/46 |
| 5,202,014 | 4/1993 | Zones et al. | 208/46 |
| 5,254,514 | 10/1993 | Nakagawa | 502/62 |
| 5,254,787 | 10/1993 | Dessau | 585/654 |
| 5,271,921 | 12/1993 | Nakagawa | 423/702 |
| 5,273,736 | 12/1993 | Nakagawa | 423/702 |
| 5,345,021 | 9/1994 | Casci et al. | 585/467 |

*Primary Examiner*—Glenn A. Caldarola
*Assistant Examiner*—Bekir L. Yildirim
*Attorney, Agent, or Firm*—R. J. Sheridan

[57] ABSTRACT

A crystalline zeolite high-silica SSZ-37 is prepared using a N,N-dimethyl-4-azoniatricyclo $[5.2.2.0^{(2,6)}]$ undec-8-ene cation as a template wherein said zeolite is used in hydrocarbon conversion processes.

38 Claims, No Drawings

HIGH-SILICA ZEOLITE SSZ-37 AND METHODS OF MAKING AND USING SAME

CROSS REFERENCE TO RELATED APPLICATION

This application is a continuation-in-part of application Ser. No. 08/380,233, filed Jan. 30, 1995, which is a continuation of Ser. No. 08/243,603, filed May. 16, 1994 (now abandoned), which is a continuation of Ser. No. 08/095,771, filed Jul. 21, 1993 (now abandoned), which is a 16 division of Ser. No. 07/906,919, filed Jun. 30, 1992 (now U.S. Pat. No. 5,254,514).

BACKGROUND OF THE INVENTION

U.S. Pat No. 5,254,514, issued Oct. 19, 1993 to Nakagawa, describes the zeolite known as "SSZ-37". The SSZ-37 is described as having a mole ratio of an oxide selected from silicon oxide, germanium oxide and mixtures thereof to an oxide selected from aluminum oxide, boron oxide, gallium oxide, iron oxide and mixtures thereof between 25:1 and 400:1 and having characteristic X-ray diffraction lines. U.S. Pat. No. 5,254,514 does not, however, disclose a high- or all-silica version of SSZ-37.

It is believed that SSZ-37 is related structurally to the zeolite designated NU-87. U.S. Pat. Nos. 5,041,402; 5,178,748 and 5,345,021, all to Casci et al., disclose NU-87. This material is said to contain equal to or less than ten moles of an oxide of aluminum, iron, gallium, boron, titanium, vanadium, zirconium, molybdenum, arsenic, antimony, chromium or manganese per 100 moles of an oxide of silicon or germanium. The typical range of the former group of oxides per 100 moles of silicon or germanium oxide is said to be in the range of 0.1 to 10, for example 0.2 to 7.5.

NU-87 is also disclosed in U.S. Pat. No. 5,102,641, issued Apr. 7, 1992 to Casci et al., with the same mole ratios of oxides as disclosed in the previously mentioned Casci et al. patents.

U.S. Pat. No. 5,254,787, issued Oct. 19, 1993 to Dessau, discloses a catalytic dehydrogenation and/or dehydrocyclization process using a Group VIA or Group VIII metal-containing non-acidic zeolite having the structure of NU-87.

SUMMARY OF THE INVENTION

In accordance with the present invention, there is provided a zeolite having a mole ratio of an oxide selected from silicon oxide, germanium oxide and mixtures thereof to an oxide selected from aluminum oxide, boron oxide, gallium oxide, iron oxide and mixtures thereof greater than 400 and having, after calcination, the X-ray diffraction lines of Table II.

Also in accordance with the present invention, there is provided a zeolite having a composition, as synthesized and in the anhydrous state, in terms of mole ratios of oxides as follows:

| | |
|---|---|
| $YO_2/W_2O_3$ | >400 |
| $Q/YO_2$ | 0.02–0.10 |
| $M_2O/YO_2$ | 0.001–0.005 | wherein M is an alkali metal cation, W is selected from aluminum, boron, gallium, iron and mixtures thereof, Y is selected from silicon, germanium and mixtures thereof, and Q is an N,N-dimethyl-4-azoniatricyclo [5.2.2.0$^{(2,6)}$] undec-8-ene cation and having the X-ray diffraction lines of Table I.

Further provided in accordance with this invention is a method for preparing a zeolite having a mole ratio of an oxide selected from silicon oxide, germanium oxide and mixtures thereof to an oxide selected from aluminum oxide, boron oxide, gallium oxide, iron oxide and mixtures thereof greater than 400 and having, after calcination, the X-ray diffraction lines of Table II, said method comprising:

(a) preparing an aqueous mixture containing sources of an alkali metal oxide, an N,N-dimethyl-4-azoniatricyclo [5.2.2.0$^{(2,6)}$] undec-8-ene cation, an oxide selected from aluminum oxide, boron oxide, gallium oxide, iron oxide and mixtures thereof, an oxide selected from silicon oxide, germanium oxide and mixtures thereof, and seed crystals of a crystalline material capable of initiating formation of said zeolite;

(b) maintaining the mixture at a temperature of at least 140° C. until crystals of said zeolite form; and (c) recovering said crystals.

The present invention also provides a process for converting hydrocarbons comprising contacting a hydrocarbonaceous feed at hydrocarbon converting conditions with a catalyst comprising a zeolite having a mole ratio of an oxide selected from silicon oxide, germanium oxide and mixtures thereof to an oxide selected from aluminum oxide, boron oxide, gallium oxide, iron oxide and mixtures thereof greater than 400 and having, after calcination, the X-ray diffraction lines of Table II.

DETAILED DESCRIPTION OF THE INVENTION

As used herein, the term "high-silica SSZ-37" refers to the zeolite SSZ-37 having a silica to alumina mole ratio of greater than 400, preferably 450 or greater, more preferably 600 or greater, more preferably 1000 or greater. The term "all-silica SSZ-37" refers to the zeolite SSZ-37 which is has only silica in its framework structure, i.e., the SSZ-37 is essentially free of other metal oxides (e.g., alumina) in the framework structure. The term "essentially free" is used because it is difficult to prepare reaction mixtures for synthesizing this material which is completely free of aluminum oxide. Especially when commercial sources of silica are used, aluminum is almost always present to a greater or lesser degree. By using "essentially free" it is meant that no aluminum or other metal is intentionally added to the reaction mixture, e.g., as an alumina or aluminate reagent, and that to the extent aluminum or another metal is present, it appears only as a contaminant in the reagents.

High-silica SSZ-37 zeolite can be suitably prepared from an aqueous solution containing sources of an alkali metal oxide, an N,N-dimethyl-4-azoniatricyclo [5.2.2.0$^{(2,6)}$] undec-8-ene cation, and the oxides indicated in Table A below. The reaction mixture should have a composition in terms of mole ratios falling within the following ranges:

TABLE A

| Reaction Mixture for High-Silica SSZ-37 | | |
|---|---|---|
| | Broad | Preferred |
| $YO_2/W_2O_3$ | >400 | ∞ |
| $OH^-/YO_2$ | 0.10–0.50 | 0.20–0.30 |
| $Q/YO_2$ | 0.10–0.30 | 0.15–0.25 |
| $M^+/YO_2$ | 0.01–0.30 | 0.05–0.15 |
| $H_2O/YO_2$ | 15–50 | 30–45 | wherein M is an alkali metal cation (preferably sodium), W is selected from aluminum, boron, gallium, iron and mixtures thereof, Y is selected from silicon, germanium and mixtures thereof, and Q is an N,N-dimethyl-4-azoniatricyclo [5.2.2.0$^{(2.6)}$] undec-8-ene cation. Anions which are associated with the organic cation are those which are not detrimental to the formation of the zeolite.

When (B)SSZ-37 is the desired product, the reaction mixture should have a composition in terms of mole ratios falling within the following ranges:

TABLE B

| Reaction Mixture for (B)SSZ-37 | | |
|---|---|---|
| | Broad | Preferred |
| $YO_2/W'_2O_3$ | >400 | ∞ |
| $YO_2/B_2O_3$ | >30 | >40 |
| $OH^-/YO_2$ | 0.10–0.50 | 0.20–0.30 |
| $Q/YO_2$ | 0.10–0.30 | 0.15–0.25 |
| $M^+/YO_2$ | 0.01–0.30 | 0.05–0.15 |
| $H_2O/YO_2$ | 15–50 | 30–45 | wherein Y, Q and M are as defined above and W' is selected from aluminum, gallium, iron and mixtures thereof.

The N,N-dimethyl-4-azoniatricyclo [5.2.2.0$^{(2.6)}$] undec-8-ene cation component Q, of the crystallization mixture, is preferably derived from a compound of the formula:

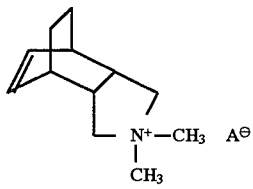

wherein A$^\ominus$ is an anion which is not detrimental to the formation of the zeolite. Representative of the anions include halogen, e.g., fluoride, chloride, bromide and iodide, hydroxide, acetate, sulfate, tetrafluoroborate, carboxylate, and the like. Hydroxide is the most preferred anion.

It has been found that the use of seed crystals in the reaction mixture is required to make high-silica SSZ-37 and (B)SSZ-37. If the above-described templating agent is used without such seed crystals, the product obtained may not be the desired one. For example, in the high-silica case, the product formed (in the absence of seed crystals) is the zeolite SSZ-31. In the boron-containing reaction, the product formed (in the absence of seed crystals) is the zeolite SSZ-33. When seed crystals are used, however, the respective products are high-silica SSZ-37 and (B)SSZ-37.

The seed crystals are crystals of crystalline materials which are capable of initiating crystallization of the zeolites of this invention from the reaction mixtures of this invention. Preferred seed crystals are SSZ-37, preferably high- or all-silica SSZ-37 or borosilicate SSZ-37. They are used in an amount ranging from about 0.1 wt % to about 10.0 wt %, preferably from about 0.5 wt % to about 5.0 wt %, based on the weight of silica used in the reaction mixture.

The reaction mixture is prepared using standard zeolitic preparation techniques, such as those described in U.S. Pat. No. 5,254,514 which is incorporated by reference in its entirety.

Typical sources of silicon oxide include silicates, silica hydrogel, silicic acid, colloidal silica, fumed silicas, tetraalkyl orthosilicates, and silica hydroxides. Typical sources of boron oxide include sodium borate and boric acid.

As-synthesized, high-silica SSZ-37 has a composition, in the anhydrous state, in terms of mole ratios, shown in Table C below.

TABLE C

| As-Synthesized High-Silica SSZ-37 | |
|---|---|
| $YO_2/W_2O_3$ | >400 |
| $Q/YO_2$ | 0.02–0.10 |
| $M_2O/YO_2$ | 0.001–0.005 | where Y, W, Q and M are as defined above.

High-silica SSZ-37 zeolite, as synthesized, has a crystalline structure whose X-ray powder diffraction pattern shows the following characteristic lines:

TABLE I

| As-synthesized high-silica SSZ-37 | | |
|---|---|---|
| 2 θ | d/n | Rel. Intensity |
| 7.03 | 12.57 | W |
| 7.82 | 11.29 | S–VS |
| 8.28 | 10.67 | W |
| 10.54 | 8.385 | W (Shoulder) |
| 12.92 | 6.847 | W |
| 19.18 | 4.623 | M |
| 20.04 | 4.426 | W–M |
| 20.42 | 4.346 | VS |
| 22.22 | 3.997 | VS |
| 22.66 | 3.921 | W |
| 23.74 | 3.745 | W |
| 25.88 | 3.440 | W–M |
| 26.57 | 3.353 | W |
| 27.12 | 3.285 | S |

The X-ray patterns such as that of Table I are based on a relative intensity scale in which the strongest line in the X-ray pattern is assigned a value of 100: W(weak) is less than 20; M(medium) is between 20 and 40; S(strong) is between 40 and 60; VS(very strong) is greater than 60.

The variation in the scattering angle (two theta) measurements, due to instrument error and to differences between individual samples, is estimated at ±0.20 degrees.

The X-ray powder diffraction patterns were determined by standard techniques. The radiation was the K-alpha/doublet of copper. The peak heights and the positions, as a function of 2θ where θ is the Bragg angle, were read from the relative intensities of the peaks, and d, the interplanar spacing in Angstroms corresponding to the recorded lines, can be calculated.

The X-ray diffraction pattern of Table I is characteristic of as-synthesized high- and all-silica SSZ-37 zeolites. The zeolite produced by exchanging some of the cations present in the zeolite with various other cations yields substantially the same diffraction pattern although there can be minor shifts in interplanar spacing and minor variations in relative intensity. Minor variations in the diffraction pattern can also result from variations in the organic compound used in the preparation. Calcination can also cause minor shifts in the X-ray diffraction pattern. Notwithstanding these minor perturbations, the basic crystal lattice structure remains unchanged.

After calcination, the high- and all-silica SSZ-37 zeolite has a crystalline structure whose X-ray powder diffraction pattern shows the following characteristic lines as indicated in Table II below:

TABLE II

Calcined All-Silica SSZ-37

| 2 θ | d/n | Rel. Intensity |
|---|---|---|
| 7.05 | 12.53 | W |
| 7.94 | 11.13 | VS |
| 8.36 | 10.57 | M |
| 10.63 | 8.313 | W (Shoulder) |
| 12.95 | 6.832 | W |
| 19.29 | 4.598 | M |
| 20.26 | 4.381 | W |
| 20.64 | 4.301 | S |
| 22.39 | 3.968 | W–M |
| 22.78 | 3.901 | W |
| 23.61 | 3.765 | W |
| 26.10 | 3.412 | W |
| 26.74 | 3.332 | W |
| 27.34 | 3.259 | W–M |

The synthetic high-silica SSZ-37 zeolite can be used as synthesized or can be thermally treated (calcined). Usually, it is desirable to remove any alkali metal cation by ion exchange and replace it with hydrogen, ammonium, or any desired metal ion. The zeolite can also be steamed; steaming helps stabilize the crystalline lattice to attack from acids. The zeolite can be used in intimate combination with hydrogenating components, such as tungsten, vanadium, molybdenum, rhenium, nickel, cobalt, chromium, manganese, or a noble metal, such as palladium or platinum, for those applications in which a hydrogenation-dehydrogenation function is desired. Typical replacing cations can include metal cations, e.g., rare earth, Group IA, Group IIA and Group VIII metals, as well as their mixtures. Of the replacing metallic cations, cations of metals such as rare earth, Fin, Ca, Mg, Zn, Ga, Cd, Pt, Pd, Ni, Co, Ti, Al, Sn, Fe and Co are particularly preferred.

The hydrogen, ammonium, and metal components can be exchanged into the zeolite. The zeolite can also be impregnated with the metals, or the metals can be physically O8 intimately admixed with the zeolite using standard methods known to the art. And, the metals can be occluded in the crystal lattice by having desired metals present as ions in the reaction mixture from which the high-silica SSZ-37 zeolite is prepared.

Typical ion exchange techniques involve contacting the synthetic zeolite with a solution containing a salt of the desired replacing cation or cations. Although a wide variety of salts can be employed, chlorides and other halides, nitrates, acetates, and sulfates are particularly preferred. Representative ion exchange techniques are disclosed in a wide variety of patents including U.S. Pat. Nos. 3,140,249; 3,140,251; and 3,140,253. Ion exchange can take place either before or after the zeolite is calcined.

Following contact with the salt solution of the desired replacing cation, the zeolite is typically washed with water and dried at temperatures ranging from 65° C. to about 315° C. After washing, the zeolite can be calcined in air or inert gas at temperatures ranging from about 200° C. to 820° C. for periods of time ranging from 1 to 48 hours, or more, to produce a catalytically active product especially useful in hydrocarbon conversion processes.

Regardless of the cations present in the synthesized form of the zeolite, the spatial arrangement of the atoms which form the basic crystal lattice of the zeolite remains essentially unchanged. The exchange of cations has little, if any, effect on the zeolite lattice structures.

The high-silica SSZ-37 can be formed into a wide variety of physical shapes and/or can be composited with other materials resistant to the temperatures and other conditions employed in organic conversion processes. See U.S. Pat. No. 5,254,514 for examples of such shapes and other materials.

High-silica SSZ-37 zeolite is useful in hydrocarbon conversion reactions. Hydrocarbon conversion reactions are chemical and catalytic processes in which carbon containing compounds are changed to different carbon containing compounds. Examples of hydrocarbon conversion reactions include catalytic cracking, hydrocracking, dewaxing, and olefin and aromatics formation reactions. The catalyst is useful in other petroleum refining and hydrocarbon conversion reactions such as isomerizing n-paraffins and naphthenes, polymerizing and oligomerizing olefinic or acetylenic compounds such as isobutylene and butene-1, reforming, alkylating, isomerizing polyalkyl substituted aromatics (e.g., meta-xylene), and disproportionating aromatics (e.g., toluene) to provide mixtures of benzene, xylenes and higher methylbenzenes. The high-silica SSZ-37 catalyst has high selectivity, and under hydrocarbon conversion conditions can provide a high percentage of desired products relative to total products.

High-silica SSZ-37 zeolite can be used in processing hydrocarbonaceous feedstocks. Hydrocarbonaceous feedstocks contain carbon compounds and can be from many different sources, such as virgin petroleum fractions, recycle petroleum fractions, shale oil, liquefied coal, tar sand oil, and, in general, can be any carbon containing fluid susceptible to zeolitic catalytic reactions. Depending on the type of processing the hydrocarbonaceous feed is to undergo, the feed can contain metal or be free of metals, it can also have high or low nitrogen or sulfur impurities. It can be appreciated, however, that in general processing will be more efficient (and the catalyst more active) the lower the metal, nitrogen, and sulfur content of the feedstock.

The conversion of hydrocarbonaceous feeds can take place in any convenient mode, for example, in fluidized bed, moving bed, or fixed bed reactors depending on the types of process desired. The formulation of the catalyst particles will vary depending on the conversion process and method of operation.

Other reactions which can be performed using the catalyst of this invention containing a metal, e.g., a Group VIII metal such platinum, include hydrogenation-dehydrogenation reactions, denitrogenation and desulfurization reactions.

High-silica SSZ-37 can be used in a hydrocarbon conversion reactions with active or inactive supports, with organic or inorganic binders, and with and without added metals. These reactions are well known to the art, as are the reaction conditions.

Hydrocracking

Using high-silica SSZ-37 catalyst which contains a hydrogenation promoter, heavy petroleum residual feedstocks, cyclic stocks and other hydrocrackate charge stocks can be hydrocracked at hydrocracking conditions including a temperature in the range of from 175° C. to 485° C., molar ratios of hydrogen to hydrocarbon charge from 1 to 100, a pressure in the range of from 0.to 350 bar, and a liquid hourly space velocity (LHSV) in the range of from 0.1 to 30.

The hydrocracking catalysts contain an effective amount of at least one hydrogenation catalyst (component) of the type commonly employed in hydrocracking catalysts. The hydrogenation component is generally selected from the group of hydrogenation catalysts consisting of one or more metals of Group VIB and Group VIII, including the salts, complexes and solutions containing such. The hydrogenation catalyst is preferably selected from the group of metals, salts and complexes thereof of the group consisting of at least one of platinum, palladium, rhodium, iridium and mixtures thereof or the group consisting of at least one of nickel, molybdenum, cobalt, tungsten, titanium, chromium and mixtures thereof. Reference to the catalytically active metal or metals is intended to encompass such metal or metals in the elemental state or in some form such as an oxide, sulfide, halide, carboxylate and the like.

The hydrogenation catalyst is present in an effective amount to provide the hydrogenation function of the hydrocracking catalyst, and preferably in the range of from 0.05 to 25% by weight.

The catalyst may be employed in conjunction with traditional hydrocracking catalysts, e.g., any aluminosilicate heretofore employed as a component in hydrocracking catalysts. Representative of the zeolitic aluminosilicates disclosed heretofore as employable as component parts of hydrocracking catalysts are Zeolite Y (including steam stabilized, e.g., ultra-stable Y), Zeolite X, Zeolite beta (U.S. Pat. No. 3,308,069), Zeolite ZK-20 (U.S. Pat. No. 3,445, 727), Zeolite ZSM-3 (U.S. Pat. No. 3,415,736), faujasite, LZ-10 (U.K. Pat. 2,014,970, Jun. 9, 1982), ZSM-5-type zeolites, e.g., ZSM-5, ZSM-11, ZSM-12, ZSM-23, ZSM-35, ZSM-38, ZSM-48, crystalline silicates such as silicalite (U.S. Pat. No. 4,061,724), erionite, mordenite, offretite, chabazite, FU-1-type zeolite, NU-type zeolites, LZ-210-type zeolite and mixtures thereof. Traditional cracking catalysts containing amounts of $Na_2O$ less than about one percent by weight are generally preferred. The relative amounts of the high-silica SSZ-37 component and traditional hydrocracking component, if any, will depend at least in part, on the selected hydrocarbon feedstock and on the desired product distribution to be obtained therefrom, but in all instances an effective amount of high-silica SSZ-37 is employed. When a traditional hydrocracking catalyst (THC) component is employed, the relative weight ratio of the THC to the high-silica SSZ-37 is generally between about 1:10 and about 500:1, desirably between about 1:10 and about 200:1, preferably between about 1:2 and about 50:1, and most preferably is between about 1:1 and about 20:1.

The hydrocracking catalysts are typically employed with an inorganic oxide matrix component which may be any of the inorganic oxide matrix components which have been employed heretofore in the formulation of hydrocracking catalysts including: amorphous catalytic inorganic oxides, e.g., catalytically active silica-aluminas, clays, silicas, aluminas, silica-aluminas, silica-zirconias, silica-magnesias, alumina-borias, alumina-titanias and the like and mixtures thereof. The traditional hydrocracking catalyst and high-silica SSZ-37 may be mixed separately with the matrix component and then mixed or the THC component and high-silica SSZ-37 may be mixed and then formed with the matrix component.

Dewaxing

High-silica SSZ-37 can be used to dewax hydrocarbonaceous feeds by selectively removing straight chain paraffins. The catalytic dewaxing conditions are dependent in large measure on the feed used and upon the desired pour point. Generally, the temperature will be between about 200° C. and about 475° C, preferably between about 250° C. and about 450° C. The pressure is typically between about 15 psig and about 3000 psig, preferably between about 200 psig and 3000 psig. The liquid hourly space velocity (LHSV) preferably will be from 0.1 to 20, preferably between about 0.2 and about 10.

Hydrogen is preferably present in the reaction zone during the catalytic dewaxing process. The hydrogen to feed ratio is typically between about 500 and about 30,000 SCF/bbl (standard cubic feet per barrel), preferably about 1000 to about 20,000 SCF/bbl. Generally, hydrogen will be separated from the product and recycled to the reaction zone. Typical feedstocks include light gas oil, heavy gas oils and reduced crudes boiling about 350° F.

The high-silica SSZ-37 hydrodewaxing catalyst may optionally contain a hydrogenation component of the type commonly employed in dewaxing catalysts. The hydrogenation component may be selected from the group of hydrogenation catalysts consisting of one or more metals of Group VIB and Group VIII, including the salts, complexes and solutions containing such metals. The preferred hydrogenation catalyst is at least one of the group of metals, salts and complexes selected from the group consisting of at least one of platinum, palladium, rhodium, iridium and mixtures thereof or at least one from the group consisting of nickel, molybdenum, cobalt, tungsten, titanium, chromium and mixtures thereof. Reference to the catalytically active metal or metals is intended to encompass such metal or metals in the elemental state or in some form such as an oxide, sulfide, halide, carboxylate and the like.

The hydrogenation component is present in an effective amount to provide an effective hydrodewaxing and hydroisomerization catalyst preferably in the range of from about 0.05 to 5% by weight.

Aromatics Formation

High-silica SSZ-37 can be used to convert light straight run naphthas and similar mixtures to highly aromatic mixtures. Thus, normal and slightly branched chained hydrocarbons, preferably having a boiling range above about 40° C. and less than about 200° C., can be converted to products having a substantial higher octane aromatics content by contacting the hydrocarbon feed with the zeolite at a temperature in the range of from about 400° C. to 600° C., preferably 480° C. to 550° C. at pressures ranging from atmospheric to 10 bar, and liquid hourly space velocities (LHSV) ranging from 0.1 to 15.

The conversion catalyst preferably contains a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. Rhenium or tin or a mixture thereof may also be used in conjunction with the Group VIII metal compound and preferably a noble metal compound. The most preferred metal is platinum. The amount of Group VIII metal present in the conversion catalyst should be within the normal range of use in reforming catalysts, from about 0.05 to 2.0 weight percent, preferably 0.2 to 0.8 weight percent.

The zeolite/Group VIII metal conversion catalyst can be used without a binder or matrix. The preferred inorganic matrix, where one is used, is a silica-based binder such as Cab-O-Sil or Ludox. Other matrices such as magnesia and titania can be used. The preferred inorganic matrix is nonacidic.

It is critical to the selective production of aromatics in useful quantities that the conversion catalyst be substantially free of acidity, for example, by poisoning the zeolite with a basic metal, e.g., alkali metal, compound. The zeolite is usually prepared from mixtures containing alkali metal hydroxides and thus have alkali metal contents of about 1–3 weight percent. These high levels of alkali metal, usually sodium or potassium, are unacceptable for most catalytic applications because they greatly deactivate the catalyst for cracking reactions. Usually, the alkali metal is removed to low levels by ion exchange with hydrogen or ammonium ions. By alkali metal compound as used herein is meant elemental or ionic alkali metals or their basic compounds. Surprisingly, unless the zeolite itself is substantially free of acidity, the basic compound is required in the present process to direct the synthetic reactions to aromatics production.

The amount of alkali metal necessary to render the zeolite substantially free of acidity can be calculated using standard techniques based on the aluminum content of the zeolite. Under normal circumstances, the zeolite as prepared and without ion exchange will contain sufficient alkali metal to neutralize the acidity of the catalyst. If a zeolite free of alkali metal is the starting material, alkali metal ions can be ion exchanged into the zeolite to substantially eliminate the acidity of the zeolite. An alkali metal content of about 100%, or greater, of the acid sites calculated on a molar basis is sufficient.

Where the basic metal content is less than 100% of the acid sites on a molar basis, the test described in U.S. Pat. No. 4,347,394 which patent is incorporated totally herein by reference, can be used to determine if the zeolite is substantially free of acidity.

The preferred alkali metals are sodium, potassium, and cesium. The zeolite itself can be substantially free of acidity only at very high silica:alumina mole ratios; by "zeolite consisting essentially of silica" is meant a zeolite which is substantially free of acidity without base poisoning.

Catalytic Cracking

Hydrocarbon cracking stocks can be catalytically cracked in the absence of hydrogen using high-silica SSZ-37 at liquid hourly space velocities from 0.5 to 50, temperatures from about 260° F. to 1625° F. and pressures from subatmospheric to several hundred atmospheres, typically from about atmospheric to about 5 atmospheres.

For this purpose, the high-silica SSZ-37 catalyst can be composited with mixtures of inorganic oxide supports as well as traditional cracking catalyst.

The catalyst may be employed in conjunction with traditional cracking catalysts, e.g., any aluminosilicate heretofore employed as a component in cracking catalysts. Representative of the zeolitic aluminosilicates disclosed heretofore as employable as component parts of cracking catalysts are Zeolite Y (including steam stabilized chemically modified, e.g., ultra-stable Y), Zeolite X, Zeolite beta (U.S. Pat. No. 3,308,069), Zeolite ZK-20 (U.S. Pat. No. 3,445,727), Zeolite ZSM-3 (U.S. Pat. No. 3,415,736), faujasite, LZ-10 (U.K. Pat. 2,014,970, Jun. 9, 1982), ZSM-5-type zeolites, e.g., ZSM-5, ZSM-11, ZSM-12, ZSM-23, ZSM-35, ZSM-38, ZSM-48, crystalline silicates such as silicalite (U.S. Pat. No. 4,061,724), erionite, mordenite, offretite, chabazite, FU-1-type zeolite, NU-type zeolites, LZ-210-type zeolite and mixtures thereof. Traditional cracking catalysts containing amounts of $Na_2O$ less than about one percent by weight are generally preferred. The relative amounts of the high-silica SSZ-37 component and traditional cracking component, if any, will depend at least in part, on the selected hydrocarbon feedstock and on the desired product distribution to be obtained therefrom, but in all instances an effective amount of high-silica SSZ-37 is employed. When a traditional cracking catalyst (TC) component is employed, the relative weight ratio of the TC to the high-silica SSZ-37 is generally between about 1:10 and about 500:1, desirably between about 1:10 and about 200:1, preferably between about 1:2 and about 50:1, and most preferably is between about 1:1 and about 20:1.

The cracking catalysts are typically employed with an inorganic oxide matrix component which may be any of the inorganic oxide matrix components which have been employed heretofore in the formulation of FCC catalysts including: amorphous catalytic inorganic oxides, e.g., catalytically active silica-aluminas, clays, silicas, aluminas, silica-aluminas, silica-zirconias, silica-magnesias, alumina-borias, alumina-titanias and the like and mixtures thereof. The traditional cracking component and high-silica SSZ-37 may be mixed separately with the matrix component and then mixed or the TC component and high-silica SSZ-37 may be mixed and then formed with the matrix component.

The mixture of a traditional cracking catalyst and high-silica SSZ-37 may be carried out in any manner which results in the coincident presence of such in contact with the crude oil feedstock under catalytic cracking conditions. For example, a catalyst may be employed containing the traditional cracking catalyst and a high-silica SSZ-37 in single catalyst particles or high-silica SSZ-37 with or without a matrix component may be added as a discrete component to a traditional cracking catalyst.

Oligomerization

High-silica SSZ-37 can also be used to oligomerize straight and branched chain olefins having from about 2 to 21 and preferably 2–5 carbon atoms. The oligomers which are the products of the process are medium to heavy olefins which are useful for both fuels, i.e., gasoline or a gasoline blending stock and chemicals.

The oligomerization process comprises contacting the olefin feedstock in the gaseous state phase with high-silica SSZ-37 at a temperature of from about 450° F. to about 1200° F., a WHSV of from about 0.2 to about 50 and a hydrocarbon partial pressure of from about 0.1 to about 50 atmospheres.

Also, temperatures below about 450° F. may be used to oligomerize the feedstock, when the feedstock is in the liquid phase when contacting the zeolite catalyst. Thus, when the olefin feedstock contacts the zeolite catalyst in the liquid phase, temperatures of from about 50° F. to about 450° F., and preferably from 80° F. to 400° F. may be used and a WHSV of from about 0.05 to 20 and preferably 0.1 to 10. It will be appreciated that the pressures employed must be sufficient to maintain the system in the liquid phase. As is known in the art, the pressure will be a function of the number of carbon atoms of the feed olefin and the temperature. Suitable pressures include from about 0 psig to about 3000 psig.

The zeolite can have the original cations associated therewith replaced by a wide variety of other cations according to techniques well known in the art. Typical cations would include hydrogen, ammonium and metal cations including mixtures of the same. Of the replacing metallic cations, particular preference is given to cations of metals such as rare earth metals, manganese, calcium, as well as metals of Group II of the Periodic Table, e.g., zinc, and Group VIII of the Periodic Table, e.g., nickel. One of the prime requisites is that the zeolite have a fairly low aromatization activity, i.e., in which the amount of aromatics produced is not more than about 20% by weight. This is accomplished by using a zeolite with controlled acid activity [alpha value] of from about 0.1 to about 120, preferably from about 0.1 to about 100, as measured by its ability to crack n-hexane.

Alpha values are defined by a standard test known in the art, e.g., as shown in U.S. Pat. No. 3,960,978 which is incorporated totally herein by reference. If required, such zeolites may be obtained by steaming, by use in a conversion process or by any other method which may occur to one skilled in this art.

High-silica SSZ-37 can be used to convert light gas $C_2$–$C_6$ paraffins and/or olefins to higher molecular weight hydrocarbons including aromatic compounds. Operating temperatures of 100° C. to 700° C., operating pressures of 0 to 1000 psig and space velocities of 0.5–40 $hr^{-1}$ WHSV (weight hourly space velocity) can be used to convert the $C_2$–$C_6$ paraffin and/or olefins to aromatic compounds. Preferably, the zeolite will contain a catalyst metal or metal oxide wherein said metal is selected from the group consisting of Groups IB, IIB, VIII and IIIA of the Periodic Table, and most preferably gallium or zinc and in the range of from about 0.05 to 5% by weight.

Condensation of Alcohols

High-silica SSZ-37 can be used to condense lower aliphatic alcohols having 1 to 10 carbon atoms to a gasoline boiling point hydrocarbon product comprising mixed aliphatic and aromatic hydrocarbon. The condensation reaction proceeds at a temperature of about 500° F. to 1000° F., a pressure of about 0.5 psig to 1000 psig and a space velocity of about 0.5 to 50 WHSV. The process disclosed in U.S. Pat. No. 3,984,107 more specifically describes the process conditions used in this process, which patent is incorporated totally herein by reference.

The catalyst may be in the hydrogen form or may be base exchanged or impregnated to contain ammonium or a metal cation complement, preferably in the range of from about 0.05 to 5% by weight. The metal cations that may be present include any of the metals of the Groups I through VIII of the Periodic Table. However, in the case of Group IA metals, the cation content should in no case be so large as to effectively inactivate the catalyst.

Isomerization

The present catalyst is highly active and highly selective for isomerizing $C_4$ to $C_7$ hydrocarbons. The activity means that the catalyst can operate at relatively low temperature which thermodynamically favors highly branched paraffins. Consequently, the catalyst can produce a high octane product. The high selectivity means that a relatively high liquid yield can be achieved when the catalyst is run at a high octane.

The present process comprises contacting the isomerization catalyst with a hydrocarbon feed under isomerization conditions. The feed is preferably a light straight run fraction, boiling within the range of 30° F. to 250° F. and preferably from 60° F. to 200° F. Preferably, the hydrocarbon feed for the process comprises a substantial amount of $C_4$ to $C_7$ normal and slightly branched low octane hydrocarbons, more preferably $C_5$ and $C_6$ hydrocarbons.

The pressure in the process is preferably between 50 psig and 1000 psig, more preferably between 100 psig and 500 psig. The liquid hourly space velocity (LHSV) is preferably between about 1 to about 10 with a value in the range of about 1 to about 4 being more preferred. It is also preferable to carry out the isomerization reaction in the presence of hydrogen. Preferably, hydrogen is added to give a hydrogen to hydrocarbon ratio ($H_2$/HC) of between 0.5 and 10 $H_2$/HC, more preferably between 1 and 8 $H_2$/HC. The temperature is preferably between about 200° F. and about 1000° F., more preferably between 400° F. and 600° F. As is well known to those skilled in the isomerization art, the initial selection of the temperature within this broad range is made primarily as a function of the desired conversion level considering the characteristics of the feed and of the catalyst. Thereafter, to provide a relatively constant value for conversion, the temperature may have to be slowly increased during the run to compensate for any deactivation that occurs.

A low sulfur feed is especially preferred in the present process. The feed preferably contains less than 10 ppm, more preferably less than 1 ppm, and most preferably less than 0.1 ppm sulfur. In the case of a feed which is not already low in sulfur, acceptable levels can be reached by hydrogenating the feed in a presaturation zone with a hydrogenating catalyst which is resistant to sulfur poisoning. An example of a suitable catalyst for this hydrodesulfurization process is an alumina-containing support and a minor catalytic proportion of molybdenum oxide, cobalt oxide and/or nickel oxide. A platinum on alumina hydrogenating catalyst can also work. In which case a sulfur sorber is preferably placed downstream of the hydrogenating catalyst, but upstream of the present isomerization catalyst. Examples of sulfur sorbers are alkali or alkaline earth metals on porous refractory inorganic oxides, zinc, etc. Hydrodesulfurization is typically conducted at 315° C. to 455° C., at 200 psig to 2000 psig, and at a liquid hourly space velocity of 1 to 5.

It is preferable to limit the nitrogen level and the water content of the feed. Catalysts and processes which are suitable for these purposes are known to those skilled in the art.

After a period of operation, the catalyst can become deactivated by sulfur or coke. Sulfur and coke can be removed by contacting the catalyst with an oxygen-containing gas at an elevated temperature. If the Group VIII metal(s) have agglomerated, then it can be redispersed by contacting the catalyst with a chlorine gas under conditions effective to redisperse the metal(s). The method of regenerating the catalyst may depend on whether there is a fixed bed, moving bed, or fluidized bed operation. Regeneration methods and conditions are well known in the art.

The conversion catalyst preferably contains a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. Rhenium and tin may also be used in conjunction with the noble metal. The most preferred metal is platinum. The amount of Group VIII metal present in the conversion catalyst should be within the normal range of use in isomerizing catalysts, from about 0.05 to 2.0 weight percent, preferably 0.2 to 0.8 weight percent.

Alkylation and Transalkylation

High-silica SSZ-37 can be used in a process for the alkylation or transalkylation of an aromatic hydrocarbon. The process comprises contacting the aromatic hydrocarbon with a $C_2$ to $C_{16}$ olefin alkylating agent or a polyalkyl aromatic hydrocarbon transalkylating agent, under at least partial liquid phase conditions, and in the presence of a catalyst comprising high-silica SSZ-37.

For high catalytic activity, the high-silica SSZ-37 zeolite should be predominantly in its hydrogen ion form.

Generally, the zeolite is converted to its hydrogen form by ammonium exchange followed by calcination. If the zeolite is synthesized with a high enough ratio of organo-nitrogen cation to sodium ion, calcination alone may be sufficient. It is preferred that, after calcination, at least 80% of the cation sites are occupied by hydrogen ions and/or rare earth ions.

The pure high-silica SSZ-37 zeolite may be used as a catalyst, but generally it is preferred to mix the zeolite powder with an inorganic oxide binder such as alumina, silica, silica/alumina, or naturally occurring clays and form the mixture into tablets or extrudates. The final catalyst may contain from 1 to 99 weight percent high-silica SSZ-37 zeolite. Usually the zeolite content will range from 10 to 90 weight percent, and more typically from 60 to 80 weight percent. The preferred inorganic binder is alumina. The mixture may be formed into tablets or extrudates having the desired shape by methods well known in the art.

Examples of suitable aromatic hydrocarbon feedstocks which may be alkylated or transalkylated by the process of the invention include aromatic compounds such as benzene, toluene and xylene. The preferred aromatic hydrocarbon is benzene. Mixtures of aromatic hydrocarbons may also be employed.

Suitable olefins for the alkylation of the aromatic hydrocarbon are those containing 2 to 4 carbon atoms, such as ethylene, propylene, butene-1, trans-butene-2 and cis-butene-2, or mixtures thereof. The preferred olefin is propylene. These olefins may be present in admixture with the corresponding $C_2$ to $C_4$ paraffins, but it is preferable to remove any dienes, acetylenes, sulfur compounds or nitrogen compounds which may be present in the olefin feedstock stream, to prevent rapid catalyst deactivation. Longer chain alpha olefins may be used as well.

When transalkylation is desired, the transalkylating agent is a polyalkyl aromatic hydrocarbon containing two or more alkyl groups that each may have from 2 to about 4 carbon atoms. For example, suitable polyalkyl aromatic hydrocarbons include di-, tri- and tetra-alkyl aromatic hydrocarbons, such as diethylbenzene, triethylbenzene, diethylmethylbenzene (diethyltoluene), di-isopropylbenzene, di-isopropyltoluene, dibutylbenzene, and the like. Preferred polyalkyl aromatic hydrocarbons are the dialkyl benzenes. A particularly preferred polyalkyl aromatic hydrocarbon is di-isopropylbenzene.

Reaction products which may be obtained include ethylbenzene from the reaction of benzene with either ethylene or polyethylbenzenes, cumene from the reaction of benzene with propylene or polyisopropylbenzenes, ethyltoluene from the reaction of toluene with ethylene or polyethyltoluenes, cymenes from the reaction of toluene with propylene or polyisopropyltoluenes, and sec-butylbenzene from the reaction of benzene and n-butenes or polybutylbenzenes. The production of cumene from the alkylation of benzene with propylene or the transalkylation of benzene with di-isopropylbenzene is especially preferred.

When alkylation is the process conducted, reaction conditions are as follows. The aromatic hydrocarbon feed should be present in stoichiometric excess. It is preferred that molar ratio of aromatics to olefins be greater than four-to-one to prevent rapid catalyst fouling. The reaction temperature may range from 100° F. to 600° F., preferably 250° F. to 450° F. The reaction pressure should be sufficient to maintain at least a partial liquid phase in order to retard catalyst fouling. This is typically 50 psig to 1000 psig depending on the feedstock and reaction temperature. Contact time may range from 10 seconds to 10 hours, but is usually from 5 minutes to an hour. The weight hourly space velocity (WHSV), in terms of grams (pounds) of aromatic hydrocarbon and olefin per gram (pound) of catalyst per hour, is generally within the range of about 0.5 to 50.

When transalkylation is the process conducted, the molar ratio of aromatic hydrocarbon will generally range from about 1:1 to 25:1, and preferably from about 2:1 to 20:1. The reaction temperature may range from about 100° F. to 600° F., but it is preferably about 250° F. to 450° F. The reaction pressure should be sufficient to maintain at least a partial liquid phase, typically in the range of about 50 psig to 1000 psig, preferably 300 psig to 600 psig. The weight hourly space velocity will range from about 0.1 to 10.

High-silica SSZ-37 can also be used as a selective adsorbent for hydrocarbons and as a water-softening agent in detergents.

The present invention will be more fully understood by reference to the following examples. They are intended to be purely exemplary and are not intended to limit the scope of the invention in any way.

The template of Example 1 is prepared by using a Diels-Alder reaction scheme. Two new bonds and a six-membered ring are formed in the Diels-Alder reaction, formally a [4+2] cyclo addition of a 1,4-conjugated diene with a double bond (dienophile). The co-pending application entitled "Method for Preparing Crystalline Materials Using Aza-Polycyclic Templating Agents", U.S. Ser. No. 907,419, filed Jun. 30, 1992, now U.S. Pat. No. 5,281,407, issued Jan. 25, 1994, describes the use of Diels-Alder chemistry to efficiently synthesize templates for zeolite synthesis. This application is incorporated by reference in its entirety.

EXAMPLES

Example 1

Synthesis of Template

772 Grams of toluene were mixed with 99.34 grams of N-methylmaleimide. 72.40 Grams of 1,3-cyclohexadiene was added dropwise over a 2-minute period while stirring using a magnetic stir bar. The reaction was heated overnight and monitored by thin layer chromatography on silica (20% EtOAc/hex). TLC indicated the reaction was complete, and therefore it was worked up. Work up consisted of transferring a mixture to a separatory funnel and adding 200 mL of $H_2O$. The pH was adjusted to $\leq 2$ with conc. HCl which gave a slight emulsion. The phases were separated. Another 200 mL of $H_2O$ was added to the organic layer and the aqueous layer was adjusted to pH $\geq 12$ with 50% NaOH solution. Phases were separated and the organic phase was dried over $MgSO_4$. Solids were filtered and the solution concentrated to yield a white solid (162.95 grams, 95.7%), designated.

A 5-liter flask was equipped with a mechanical stirrer, reflux condenser, addition funnel, $N_2$ inlet, and $N_2$ outlet. This reaction was run under $N_2$ atmosphere. The reaction flask was charged with lithium aluminum hydride (102.06 grams, 2.55 mol) and 2413 mL of anhydrous diethyl ether. The addition funnel was charged with the imide from the Diels-Alder reaction (162.85 grams, 0.85 mol) and 1206 mL of methylene chloride. The reaction vessel was cooled in an acetone/dry ice bath (−78° C.) and the imide solution was added to the lithium aluminum hydride solution over 30 minutes. Dry ice was added to the cooling bath to control the exotherm of the reaction. The grey heterogeneous reaction mixture was stirred at room temperature and monitored by thin layer chromatography on silica (40% EtOAc/hex). It was stirred overnight at room temperature.

TLC indicated the reaction was complete, therefore the reaction was worked up. 93.2 mL of $H_2O$ were cautiously added to the reaction mixture to decompose the lithium aluminum hydride. This generates hydrogen. This was followed by the slow addition of 93.2 mL of 15% of aq. NaOH. The ether which evaporated was replaced by methylene chloride. Another 280.2 mL of $H_2O$ was added and the reaction mixture turned from grey to white. This suspension was stirred for 30 minutes at room temperature, and then the solids were removed by vacuum filtration. Solids were washed with methylene chloride. The filtrate was transferred to a 6-liter separatory funnel, and 300 mL of $H_2O$ were added. The aqueous layer was adjusted to pH $\leq 2$ with conc. HCl. The phases were separated and another acidic wash was performed. The combined acidic aqueous layers were then adjusted to pH $\geq 12$ with 50% NaOH solution and saturated with NaCl. This was then extracted four times with 250 mL of ether. The combined organic extracts were dried over $Na_2SO_4$, filtered and concentrated to yield 104.89 grams (75.6%) of the amine.

This amine was dissolved in 643 mL of chloroform in a 2-liter flask which was equipped with a magnetic stirrer and addition funnel. This was cooled in an ice/water bath and methyl iodide (183.9 grams, 1.28 mol) was added over a 60-minute period. The reaction was stirred at room temperature for 4 days, then transferred to an addition funnel. The solution was added dropwise to 2 liters of stirring diethyl ether. The yellow solids were collected by filtration and recrystallized from hot acetone/diethyl ether with a small amount of methanol to afford white crystals of the desired product (180.39 grams, 92.3%). The melting point was determined to be 234° C.-236° C. The C, H and N values were measured as C, 47.30; H, 6.64; and N, 4.50.

Example 2

140.07 Grams of a 0.46 mol of the product of Example 1 was ion-exchanged with 315 grams of a hydroxide ion-exchange resin (BioRad AG 1-X8) and 400 cc of water to form the hydroxide form of this template. The mixture was stirred overnight at room temperature. The solids were removed by filtration and washed. The solution was titrated to determine molarity.

Example 3

Synthesis of All-Silica SSZ-37

The template prepared in Example 2 (2.57 grams of a 0.58M OH solution), 1.0 gram of 1.0N NaOH, 4.34 grams of deionized water and 0.62 gram of Cabosil M5 fumed silica were mixed in a 25 ml Teflon cup for a Parr 4645 reactor. Seed crystals of high-silica SSZ-37 (0.03 gram, starting silica/alumina mole ratio =200) were then added and the resulting mixture was sealed and heated at 150° C. (static) for seven days, after which a settled product was obtained. The solids were filtered, washed thoroughly with water, dried and determined by X-ray diffraction (XRD) to be all-silica SSZ-37.

Example 4

Synthesis of All-Silica SSZ-37

The template prepared in Example 2 (3.68 grams of a 0.61M OH solution), 1.5 grams of 1.0N KOH, 5.61 grams of deionized water and 0.92 gram of Cabosil M5 fumed silica were mixed in a 25 ml Teflon cup for a Parr 4645 reactor. Seed crystals of all-silica SSZ-37 from Example 3 (0.01 gram) were then added and the resulting mixture was sealed and heated at 160° C. and tumbled at a rate of 54 rpm. After seven days, a settled product was obtained which was filtered, washed thoroughly with water, dried and determined by XRD to be all-silica SSZ-37.

The table below shows XRD lines for the material prepared in this example.

| 2 θ | d/n | 100 × $I/I_o$ |
| --- | --- | --- |
| 7.03 | 12.57 | 4 |
| 7.82 | 11.29 | 60 |
| 8.28 | 10.67 | 14 |
| 10.54 | 8.385 | 3 (Shoulder |
| 12.92 | 6.847 | 7 |
| 19.18 | 4.623 | 31 |
| 20.04 | 4.426 | 20 |
| 20.42 | 4.346 | 100 |
| 22.22 | 3.997 | 70 |
| 22.66 | 3.921 | 18 |
| 23.74 | 3.745 | 14 |
| 25.88 | 3.440 | 20 |
| 26.57 | 3.353 | 19 |
| 27.12 | 3.285 | 42 |

I represents the peak height. 100 X $I/I_o$ is the relative intensity of each peak, where $I_o$ is the intensity of the strongest line or peak.

Example 5

Synthesis of (B)SSZ-37 Using Boric Acid

The template prepared in Example 2 (5.15 grams of a 0.58M OH solution), 0.75 gram of a 1.0N NaOH solution, 4.89 grams of deionized water and 0.019 gram of boric acid were mixed together until the solids dissolved. Cabosil M5 fumed silica (0.92 gram) was added with stirring, followed by 0.03 gram of high-silica SSZ-37 (0.03 gram, starting silica/alumina mole ratio =200) and the reactor was sealed and heated at 170° C. and tumbled at a rate of 43 rpm. After seven days, a settled product was obtained and determined by XRD to be borosilicate SSZ-37. This product was found to have a $SiO_2/B_2O_3$ mole ratio of 71.

Example 6

Synthesis of (B)SSZ-37 Using Sodium Borate

The template prepared in Example 2 (3.68 grams of a 0.61M OH solution), 1.95 grams of a 1.0N NaOH solution, 5.16 grams of deionized water and 0.057 gram of sodium borate decahydrate were mixed together until the solids dissolved. Cabosil M5 fumed silica (0.92 gram) was added with stirring, followed by 0.01 gram of (B)SSZ-37 seed crystals from Example 5. The reactor was sealed and heated at 160° C. and tumbled at a rate of 43 rpm. After 13 days, a settled product was obtained which was filtered, washed, dried and determined by XRD to be borosilicate SSZ-37. This product was found to have a $SiO_2/B_2O_3$ mole ratio of 46.

XRD lines for the product of this example are provided in the table below.

| 2 θ | d/n | 100 × $I/I_o$ |
| --- | --- | --- |
| 7.04 | 12.54 | 3 |
| 7.86 | 11.25 | 86 |

-continued

| 2 θ | d/n | 100 × I/I₀ |
|---|---|---|
| 8.32 | 10.62 | 16 |
| 10.55 | 8.377 | 3 |
| 12.94 | 6.836 | 6 |
| 19.27 | 4.603 | 40 |
| 20.21 | 4.390 | 29 |
| 20.46 | 4.337 | 100 |
| 22.31 | 3.981 | 70 |
| 22.73 | 3.909 | 23 |
| 23.80 | 3.735 | 25 |
| 26.03 | 3.420 | 18 |
| 26.71 | 3.334 | 14 |
| 27.25 | 3.270 | 36 |

The following examples illustrate that if the template which is used to prepare NU-87 (decamethonium hydroxide) is substituted for the template of this invention in the type of reactions which yield all-silica SSZ-37 or (B)SSZ-37 when the template of this invention is used, the product which is obtained is ZSM-48.

Comparative Example A

The procedure described in Example 6 was repeated, with the exception that 2.82 grams of a 0.08M solution of decamethonium hydroxide was used as the templating agent instead of the template of example 2. After eight days at 160° C. (43 rpm), settled product was obtained which was determined by XRD to be borosilicate ZSM-48.

Comparative Example B

Decamethonium hydroxide (2.82 9rams of a 0.8M solution), 6.47 grams of deionized water, 1.5 9rams of a 1.0N NaOH solution and 0,037 gram of boric acid were mixed together until the solids dissolved. Cabosil M5 fumed silica (0.92 gram) was added with stirring, followed by 0.01 gram of (B)SSZ-37 seed crystals (from Example 5). The reaction mixture was sealed and heated to 160° C. and tumbled at 43 rpm. After 12 days, the solids which had formed were isolated and determined by XRD to be borosilicate ZSM-48 with some amorphous material.

Comparative Example C

Decamethonium hydroxide (2.82 grams of a 0.8M solution), 6.47 grams of deionized water, 1.5 grams of a 1.0N KOH solution and Cabosil M5 fumed silica (0.92 gram) were mixed together until a homogeneous solution was obtained. The reaction mixture was sealed and heated to 160° C. (static) for seven days, after which a settled product was obtained. The product was determined by XRD to be ZSM-48.

Example 7

Calcination of All-Silica SSZ-37

The crystalline products of Examples 3 and 4 were subjected to calcination as follows. The samples were heated in a muffle furnace from room temperature to 120° C. at a rate of 1° C./minute. The temperature was held at 120° C. for three hours, after which the temperature was increased to 540° C. at a rate of 1° C./minute. After holding at 540° C. for five hours, the temperature was ramped at the same rate to 595° C., and then held for another five hours. A 50/50 mixture of air and nitrogen was passed over the zeolite at a rate of 20 standard cubic feet per minute during heating.

The material obtained following this treatment was found to have a cyclohexane micropore volume of 0.11 cc/g at $p/p_o$=0.13.

XRD lines for the calcined product of Example 4 are provided in the table below.

| 2 θ | d/n | 100 × I/I₀ |
|---|---|---|
| 7.05 | 12.53 | 6 |
| 7.94 | 11.13 | 100 |
| 8.36 | 10.57 | 22 |
| 10.63 | 8.313 | 8 |
| 12.95 | 6.832 | 8 |
| 19.29 | 4.598 | 26 |
| 20.26 | 4.381 | 7 |
| 20.64 | 4.301 | 53 |
| 22.39 | 3.968 | 20 |
| 22.78 | 3.901 | 2 |
| 23.61 | 3.765 | 2 |
| 26.10 | 3.412 | 7 |
| 26.74 | 3.332 | 6 |
| 27.34 | 3.259 | 24 |

Example 8

Treatment of All-Silica SSZ-37 With Pt 6.2 Grams of deionized water, 0.62 gram of 0.15N NH₄OH solution and 0.62 gram of calcined all-silica SSZ-37 were mixed together with stirring. 0.34 Gram of a 0.05M Pt(NH₃)₄(NO₃)₂ solution was added dropwise to the heterogeneous mixture and the resulting mixture was stirred overnight at room temperature, filtered, and washed thoroughly with water. The dried product was then calcined to 288° C. for three hours in air. This exchange treatment was designed to yield 0.5 wt % Pt on the catalyst.

Example 9

Constraint Index and Activity of All-silica Pt-SSZ-37

The platinum-exchanged sample from Example 8 was pelleted at 2–3 KPSI, crushed and meshed to 20–40, and then 0.50 grams was dried at 400° F. in air for 4 hours and cooled in desiccator. 0.47 Gram was packed into a ⅜" stainless steel tube with alundum on both sides of the zeolite bed. A Lindburg furnace was used to heat the reactor tube. Helium was introduced into the reactor tube at 9.4 cc/min. and atmospheric pressure. The reactor was taken to 800° F., and a 50/50, w/w feed of n-hexane and 3-methylpentane was introduced into the reactor at a rate of 8 μl/min. Feed delivery was made via a piston pump. Direct sampling onto a gas chromatograph began after introduction of the feed. The constraint index value was calculated from gas chromatographic data using methods known in the art and found to be 1.6. At 800° F. and 40 minutes on-stream, feed conversion was greater than 45%. The product selectivities shown in the table below illustrate that Pt-all-silica SSZ-37 has very high aromatization and dehydrogenation activity and selectivity.

| | 10 minutes | 40 minutes | 430 minutes |
|---|---|---|---|
| Feed conversion % | 57.4 | 47.8 | 32.9 |
| Product Selectivities | | | |
| C6 Isomerization | 3.7 | 2.9 | 1.5 |
| C5-Cracking | 11.2 | 8.1 | 3.6 |
| Aromatization | 39.6 | 36.2 | 27.5 |
| Dehydrogenation | 28.2 | 35.5 | 49.6 |

What is claimed is:

1. A zeolite having a mole ratio of an oxide selected from silicon oxide, germanium oxide and mixtures thereof to an oxide selected from aluminum oxide, boron oxide, gallium oxide, iron oxide and mixtures thereof greater than 400 and having, after calcination, the X-ray diffraction lines of Table II.

2. A zeolite having a composition, as synthesized and in the anhydrous state, in terms of mole ratios of oxides as follows:

| | |
|---|---|
| $YO_2/W_2O_3$ | >400 |
| $Q/YO_2$ | 0.02–0.10 |
| $M_2O/YO_2$ | 0.001–0.005 | wherein M is an alkali metal cation, W is selected from aluminum, boron, gallium, iron and mixtures thereof, Y is selected from silicon, germanium and mixtures thereof, and Q is an N,N-dimethyl-4-azoniatricyclo [5.2.2.0$^{(2,6)}$] undec-8-ene cation and having the X-ray diffraction lines of Table I.

3. The zeolite according to claim 1 or 2 wherein W is aluminum and Y is silicon.

4. The zeolite according to claim 1 or 2 wherein said mole ratio of silicon oxide or germanium oxide to aluminum oxide, gallium oxide, or iron oxide is 450 or greater.

5. The zeolite according to claim 1 or 2 wherein said mole ratio of silicon oxide or germanium oxide to aluminum oxide, gallium oxide, or iron oxide is 600 or greater.

6. The zeolite according to claim 1 or 2 wherein said mole ratio of silicon oxide or germanium oxide to aluminum oxide, gallium oxide, or iron oxide is 1000 or greater.

7. The zeolite according to claim 1 or 2 which is essentially free of oxides selected from aluminum oxide, boron oxide, gallium oxide and iron oxide.

8. A zeolite according to claim 1 which has undergone ion exchange with hydrogen, ammonium, rare earth metal, Group IIA metal, or Group VIII metal ions.

9. A zeolite according to claim 1 wherein rare earth metals, Group IIA metals, or Group VIII metals are occluded in the zeolite.

10. A method for preparing a zeolite having a mole ratio of an oxide selected from silicon oxide, germanium oxide and mixtures thereof to an oxide selected from aluminum oxide, boron oxide, gallium oxide, iron oxide and mixtures thereof greater than 400 and having, after calcination, the X-ray diffraction lines of Table II, said method comprising:

(a) preparing an aqueous mixture containing sources of an alkali metal oxide, an N,N-dimethyl-4-azoniatricyclo [5.2.2.0$^{(2,6)}$] undec-8-ene cation, an oxide selected from aluminum oxide, boron oxide, gallium oxide, iron oxide and mixtures thereof, an oxide selected from silicon oxide, germanium oxide and mixtures thereof, and seed crystals of a crystalline material capable of initiating formation of said zeolite;

(b) maintaining the mixture at a temperature of at least 140° C. until crystals of said zeolite form; and (c) recovering said crystals.

11. The method according to claim 10 wherein the aqueous mixture has a composition in terms of mole ratios falling in the ranges:

$YO_2/W_2O_3 > 400$ $OH^-/YO_2 \, 0.10–0.50$ $Q/YO_2 \, 0.10–0.30$ $M^+/YO_2 \, 0.01–0.30$ $H_2O/YO_2 \, 15–50$ wherein Q is N,N-dimethyl-4-azoniatricyclo [5.2.2.0$^{(2,6)}$] undec-8-ene, Y is selected from silicon, germanium and mixtures thereof, W is selected from aluminum, boron, gallium, iron and mixtures thereof, and M is an alkali metal cation.

12. The method according to claim 11 wherein the aqueous mixture has a composition in terms of mole ratios falling in the ranges:

| | |
|---|---|
| $YO_2/W_2O_3$ | ∞ |
| $OH^-/YO_2$ | 0.20–0.30 |
| $Q/YO_2$ | 0.15–0.25 |
| $M^+/YO_2$ | 0.05–0.15 |
| $H_2O/YO_2$ | 30–45 |

13. The method according to claim 11 wherein the zeolite is a borosilicate and the aqueous mixture has a composition in terms of mole ratios falling in the ranges:

$YO_2/W'_2O_3 > 400$ $YO_2/B_2O_3 > 400$ $OH^-/YO_2 \, 0.10–0.5$.

$Q/YO_2 \, 0.10–0.30$ $M^+/YO_2 \, 0.01–0.30$ $H_2O/YO_2 \, 15–50$ wherein Y, Q and M are as defined in claim 11 and W' is selected from aluminum, gallium, iron and mixtures thereof.

14. The method according to claim 13 wherein the aqueous mixture has a composition in terms of mole ratios falling in the ranges:

| | |
|---|---|
| $YO_2/W'_2O_3$ | ∞ |
| $YO_2/B_2O_3$ | >40 |
| $OH^-/YO_2$ | 0.20–0.30 |
| $Q/YO_2$ | 0.15–0.25 |
| $M^+/YO_2$ | 0.05–0.15 |
| $H_2O/YO_2$ | 30–45 |

15. The method according to claim 11 wherein Y is silicon and W is aluminum.

16. A process for converting hydrocarbons comprising contacting a hydrocarbonaceous feed at hydrocarbon converting conditions with a catalyst comprising a zeolite having a mole ratio of an oxide selected from silicon oxide, germanium oxide and mixtures thereof to an oxide selected from aluminum oxide, boron oxide, gallium oxide, iron oxide and mixtures thereof greater than 400 and having, after calcination, the X-ray diffraction lines of Table II.

17. The process of claim 16 which is a hydrocracking process comprising contacting the hydrocarbon feedstock under hydrocracking conditions with a catalyst comprising a zeolite having a mole ratio of an oxide selected from silicon oxide, germanium oxide and mixtures thereof to an oxide selected from aluminum oxide, boron oxide, gallium oxide, iron oxide and mixtures thereof greater than 400 and having, after calcination, the X-ray diffraction lines of Table II and a Group VIII metal.

18. The process of claim 16 which is a dewaxing process comprising contacting the hydrocarbon feedstock under dewaxing conditions with a catalyst comprising a zeolite having a mole ratio of an oxide selected from silicon oxide, germanium oxide and mixtures thereof to an oxide selected from aluminum oxide, boron oxide, gallium oxide, iron oxide and mixtures thereof greater than 400 and having, after calcination, the X-ray diffraction lines of Table II.

19. The process of claim 16 which is a process for preparing a high octane product having an increased aromatics content comprising:

(a) contacting a hydrocarbonaceous feed which comprises normal and slightly branched hydrocarbons having a boiling range above about 40° C. and less than about 200° C., under aromatic conversion conditions with a catalyst comprising a zeolite having a mole ratio of an oxide selected from silicon oxide, germanium oxide and mixtures thereof to an oxide selected from aluminum oxide, boron oxide, gallium oxide, iron oxide and mixtures thereof greater than 400 and having, after calcination, the X-ray diffraction lines of Table II, wherein said zeolite is substantially free of acidity; and (b) recovering a product with higher octane and higher aromatic content.

20. The process of claim 19 wherein the zeolite contains a Group VIII metal component.

21. The process of claim 16 which is a catalytic cracking process comprising the step of contacting the hydrocarbon feedstock in a reaction zone under catalytic cracking conditions in the absence of added hydrogen with a catalyst comprising a zeolite having a mole ratio of an oxide selected from silicon oxide, germanium oxide and mixtures thereof to an oxide selected from aluminum oxide, boron oxide, gallium oxide, iron oxide and mixtures thereof greater than 400 and having, after calcination, the X-ray diffraction lines of Table II.

22. The process according to claim 21 wherein the catalyst contains a large pore size crystalline aluminosilicate cracking component.

23. The process of claim 16 which is an isomerizing process for isomerizing $C_4$ to $C_7$ hydrocarbons, comprising contacting a catalyst, comprising at least one Group VIII metal and a zeolite having a mole ratio of an oxide selected from silicon oxide, germanium oxide and mixtures thereof to an oxide selected from aluminum oxide, boron oxide, gallium oxide, iron oxide and mixtures thereof greater than 400 and having, after calcination, the X-ray diffraction lines of Table II, with a feed having normal and slightly branched $C_4$ to $C_7$ hydrocarbons under isomerization conditions.

24. A process in accordance with claim 23 wherein the catalyst has been calcined in a steam/air mixture at an elevated temperature after impregnation of the Group VIII metal.

25. A process in accordance with claim 24 wherein the Group VIII metal is platinum.

26. The process of claim 16 which is a process for alkylating an aromatic hydrocarbon which comprises contacting under alkylating conditions at least a mole excess of an aromatic hydrocarbon with a $C_2$ to $C_4$ olefin under at least partial liquid phase conditions and in the presence of a catalyst comprising a zeolite having a mole ratio of an oxide selected from silicon oxide, germanium oxide and mixtures thereof to an oxide selected from aluminum oxide, boron oxide, gallium oxide, iron oxide and mixtures thereof greater than 400 and having, after calcination, the X-ray diffraction lines of Table II.

27. The process of claim 26 wherein the aromatic hydrocarbon and olefin are present in a molar ratio of about 4:1 to 20:1, respectively.

28. The process of claim 26 wherein the aromatic hydrocarbon is a member selected from the group consisting of benzene, toluene and xylene, or mixtures thereof.

29. The process of claim 16 which is a process for transalkylating an aromatic hydrocarbon which comprises contacting under transalkylating condition an aromatic hydrocarbon with a polyalkyl aromatic hydrocarbon under at least partial liquid phase conditions and in the presence of a catalyst comprising a zeolite having a mole ratio of an oxide selected from silicon oxide, germanium oxide and mixtures thereof to an oxide selected from aluminum oxide, boron oxide, gallium oxide, iron oxide and mixtures thereof greater than 400 and having, after calcination, the X-ray diffraction lines of Table II.

30. The process of claim 29 wherein said aromatic hydrocarbon and said polyalkyl aromatic hydrocarbon are present in a molar ratio of about 1:1 to about 25:1, respectively.

31. The process of claim 29 wherein the aromatic hydrocarbon is a member selected from the group consisting of benzene, toluene and xylene, or mixtures thereof.

32. The process of claim 29 wherein the polyalkyl aromatic hydrocarbon is dialkylbenzene.

33. A process in accordance with claim 16 wherein the process comprises:

(a) contacting a hydrocarbonaceous feed, which comprises normal and slightly branched hydrocarbons having a boiling range above about 40° C. and less than about 200° C. under aromatic conversion conditions with a catalyst comprising a zeolite having a mole ratio of an oxide selected from silicon oxide, germanium oxide and mixtures thereof to an oxide selected from aluminum oxide, boron oxide, gallium oxide, iron oxide and mixtures thereof greater than 400 and having, after calcination, the X-ray diffraction lines of Table II; and (b) recovering an aromatic-containing effluent.

34. The process in accordance with claim 16 wherein the process is a process for converting a $C_2$–$C_6$ olefin or paraffin feedstream to aromatic compounds comprising contacting the feed material under aromatic conversion conditions with a catalyst comprising a zeolite having a mole ratio of an oxide selected from silicon oxide, germanium oxide and mixtures thereof to an oxide selected from aluminum oxide, boron oxide, gallium oxide, iron oxide and mixtures thereof greater than 400 and having, after calcination, the X-ray diffraction lines of Table II.

35. The process of claim 16 which is an isomerization process for isomerizing xylenes, comprising contacting a catalyst, comprising at least one Group VIII metal and a zeolite having a mole ratio of an oxide selected from silicon oxide, germanium oxide and mixtures thereof to an oxide selected from aluminum oxide, boron oxide, gallium oxide, iron oxide and mixtures thereof greater than 400 and having, after calcination, the X-ray diffraction lines of Table II, with a hydrocarbon feed having xylenes under isomerization conditions.

36. The process of claim 16 which is a dehydrogenation process for the dehydrogenation of alkanes, comprising contacting an alkane, under dehydrogenation conditions, with a catalyst comprising at least one Group VIII metal and a zeolite having a mole ratio of an oxide selected from silicon oxide, germanium oxide and mixtures thereof to an oxide selected from aluminum oxide, boron oxide, gallium oxide, iron oxide and mixtures thereof greater than 400 and having, after calcination, the X-ray diffraction lines of Table II.

37. A process for the conversion of lower aliphatic alcohols having 1 to 8 carbon atoms to form gasoline boiling range hydrocarbons which comprises contacting the alcohols under converting conditions with a catalyst comprising a zeolite having a mole ratio of an oxide selected from silicon oxide, germanium oxide and mixtures thereof to an oxide selected from aluminum oxide, boron oxide, gallium oxide, iron oxide and mixtures thereof greater than 400 and having, after calcination, the X-ray diffraction lines of Table II.

38. The process of claim 37 wherein the alcohol is methanol.

* * * * *